United States Patent [19]

Nakano et al.

[11] Patent Number: 5,349,067
[45] Date of Patent: Sep. 20, 1994

[54] METHOD FOR THE SYNTHESIS OF QUATERNARY AMMONIUM SALTS

[75] Inventors: Shinji Nakano, Takatsuki; Takao Morimoto, Katano; Takeshi Endo, Yokohama, all of Japan

[73] Assignee: Nippon Paint Co., Ltd., Osaka, Japan

[21] Appl. No.: 45,540

[22] Filed: Apr. 9, 1993

[30] Foreign Application Priority Data

Apr. 10, 1992 [JP] Japan .................................. 4-117929

[51] Int. Cl.$^5$ .................. C07D 211/10; C07D 211/18; C07D 211/26
[52] U.S. Cl. ..................................... 546/347; 562/84; 564/282
[58] Field of Search .......................... 546/347; 562/84; 564/282

[56] References Cited

PUBLICATIONS

*Theilheimer's Synthetic Methods of Organic Chemistry*, vol. 36 p. 54, 1982.
Theirheimer's Synthetic Methods of Organic Chemistry, vol. 16 p. 17, 1962.

*Primary Examiner*—C. Warren Ivy
*Assistant Examiner*—D. Margaret M. Mach
*Attorney, Agent, or Firm*—Millen, White, Zelano, & Branigan

[57] ABSTRACT

Provided is a convenient method for the synthesis of quaternary ammonium sulfonate compounds which are useful as curing catalysts for one-part thermosetting resin compositions which maintain storage stability at room temperature. The compounds are synthesized by subjecting in one step a benzyl alcohol optionally having on the benzene ring and/or the α-position one or more substituent groups to reaction with a corresponding tertiary amine and an organic sulfonic acid chloride.

8 Claims, No Drawings

METHOD FOR THE SYNTHESIS OF QUATERNARY AMMONIUM SALTS

BACKGROUND OF THE INVENTION

There have been disclosed quaternary ammonium salts of the class of benzylammonium sulfonate compounds in our U.S. Pat. No. 5,066,722. These compounds are useful as curing catalysts for one-part thermosetting resin compositions which are stable during storage at room temperature.

In the above cited patent literature, these compounds have been synthesized through a two step two reaction process: (a) to a conventional method for the synthesis of quaternary ammonium salts, an amine corresponding to the final product is first subjected to reaction with a corresponding benzyl halide (i.e. a quaternizing agent) to obtain a quaternary ammonium halide, (b) then, the halide anion of thus obtained quaternary ammonium halide is replaced with a desired sulfonate anion.

SUMMARY OF THE INVENTION

The present inventors searched for a convenient method for the synthesis of these compounds, and, as a result, succeeded in synthesizing the desired quaternary ammonium sulfonate compounds by subjecting in one step an amine intended to be quaternized to reaction with a corresponding benzyl alcohol and an organic sulfonic acid chloride.

It therefore is the object of the present invention to provide a convenient method for synthesizing a quaternary ammonium salt. More specifically, it is the object of the present invention to provide method for synthesizing a quaternary ammonium sulfonate compounds, characterized in that a benzyl alcohol optionally having on the benzene ring and/or at α-position one or more substituent groups inert to the intended reaction is subjected to the reaction with a tertiary amine and an organic sulfonic acid chloride.

DETAILED DISCUSSION

Among benzyl alcohols which can be used in the present method for the synthesis, the alcohols of the formula:

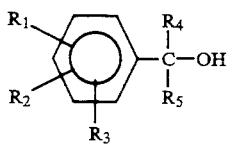

wherein $R_1$, $R_2$ and $R_3$ independently of one another denote hydrogen, hydroxyl, halogen, alkyl, alkoxy, nitro, amino, alkylamino, acyl, cyano, alkoxycarbonyl or carbamoyl, and $R_4$ and $R_5$ independently of one another denote hydrogen, halogen or alkyl, are preferred.

Among tertiary amines, the pyridines of the formula:

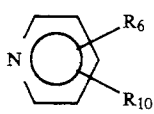

wherein $R_6$ and $R_{10}$ independently of one another denote hydrogen, hydroxyl, halogen, alkyl, alkoxy, nitro, amino, alkylamino, acyl, cyano, alkoxycarbonyl or carbamoyl, or the aniline derivatives of the formula:

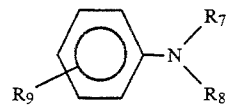

wherein $R_7$ and $R_8$ independently of one another denote alkyl or alkenyl, and $R_9$ denotes hydrogen, alkyl, halogen, nitro, cyano, amino, mono- or dialkylamino, are preferred., Among organic sulfonic acid chlorides, benzene- or naphthalenesulfonic acid chlorides optionally substituted with one or more alkyl groups are preferred.

The synthesis is attainable by subjecting a corresponding tertiary amine to the reaction with a benzyl alcohol and an organic sulfonic acid chloride in either an aprotic solvent such as benzene, toluene, ethyl acetate, butyl acetate, acetone, methyl isobutyl ketone, dichloromethane, dichloroethane, tetrahydrofuran, dioxane, nitromethane, nitrobenzene, acetonitrile and the like or in a protic solvent such as isopropanol, t-butanol and the like, at from 0° C. to the boiling temperature of the solvent. In order to remove hydrogen chloride generated as a by-product, an excess amount of the reactant tertiary amine can be used, although other secondary or tertiary amines, most preferably dicyclohexylamine or a metal alcoholate such as an alkali metal alcoholate, can be added to the reaction mixture for this purpose.

If salts other than sulfonate salts, such as salts with $AsF_6^-$, $SbF_6^-$, $BF_4^-$, $PF_6^-$, $ClO_4^-$, $FeCl_4^-$ or $CF_3SO_3^-$-ions, are desired, they can be synthesized by exchange reaction between alkali metal salts, such as sodium salts, of these anions and the sulfonate salts obtained by the aforementioned method. Thus, a compound of the formula MX (wherein M is an alkali metal, and X is $AsF_6^-$, $SbF_6^-$, $BF_4^-$, $PF_6^-$, $ClO_4^-$, $FeCl_4^-$ or $CF_3SO_3^-$ anion) is used in a conventional manner to replace said sulfonate anion of the obtained sulfonate with said $X^-$ anion.

EXAMPLES

Example 1

Synthesis of N-benzylpyridinium tosylate 19.07 g (0.1 mol) of tosyl chloride and 15.82 g (0.2 mol) of pyridine were dissolved in 60 g of acetone, and, after cooling to 5° C., there was added 10.81 g (0.1 mol) of benzyl alcohol. While suppressing excessive elevation of the temperature, reaction was allowed for 5 hours. After the completion of the reaction, the mixture was concentrated and the precipitated white solid was washed with ether and dried to give N-benzylpyridinium tosylate. Yield: 80%.

Example 2

Synthesis of N-benzyl-N,N-dimethylanilinium tosylate 19.07 g (0.1 mol) of tosyl chloride, 12.12 g (0.1 mol) of N,N-dimethylaniline and 10.1 g (0.1 mol) of triethylamine were dissolved in 60 g of tetrahydrofuran, and, after cooling to 10° C., there was added 10.81 g (0.1 mol) of benzyl alcohol. While suppressing excessive elevation of the temperature, the reaction was allowed for 5 hours. After the completion of the reaction, the mixture was concentrated, and the precipitated white solid was washed with ether and dried to give N-benzyl-N,N-dimethylanilinium tosylate. Yield: 70%.

Example 3

Synthesis of N-(4-methylbenzyl)-4-cyanopyridinium 4-dodecylbenzenesulfonate 37.9 g (0.11 mol) of dodecylbenzenesulfonyl chloride, 10.4 g (0.1 mol) of 4-cyanopyridine and 22.25 g (0.12 mol) of tributylamine were dissolved in 60 g of dichloromethane, and, after cooling to 5° C., there was added 12.21 g (0.1 mol) of 4-methylbenzylalcohol. While suppressing excessive elevation of the temperature, the reaction was allowed for 5 hours. After the completion of the reaction, the mixture was concentrated, and the precipitated white solid was washed with ether and dried to give N-(4-methylbenzyl)-4-cyanopyridinium 4-dodecylbenzenesulfonate. Yield: 73%.

Example 4

Synthesis of N-(4-methoxybenzyl)-N-ethyl-N-methylanilinium tosylate 19.07 g (0.1 mol) of tosyl chloride, 13.5 g (0.1 mol) of N-ethyl-N-methylaniline and 27.20 g (0.15 mol) of dicyclohexylamine were dissolved in 60 g of dichloromethane, and, after cooling to 5° C., there was added 13.81 g (0.1 mol) of 4-methoxybenzylalcohol. While suppressing excessive elevation of the temperature, the reaction was allowed for 6 hours. After the completion of the reaction, the mixture was concentrated, and the precipitated white solid was washed with ether and dried to give N-(4-methoxybenzyl)-N-ethyl-N-methyl-anilinium tosylate. Yield: 50%.

Example 5

Synthesis of N-(4-methylbenzyl)-N,N-dimethylanilinium 4-dodecylbenzenesulfonate 12.21 g (0.1 mol) of 4-methylbenzylalcohol was dissolved in 60 g of 1,4-dioxane, and was added while cooling to 11.22 g (0.1 mol) of potassium t-butoxide. The solution was added dropwise to a solution of 34.5 g (0.1 mol) of 4-dodecylbenzenesulfonyl chloride in 1,4-dioxane over one hour. Subsequently, 12.12 g (0.1 mol) of N,N-dimethylaniline was added and stirred at room temperature for 16 hours. After the completion of the reaction, the mixture was filtered and concentrated, and the precipitated solid was washed with ether and dried to give the titled compound. Yield: 53%.

Example 6

Synthesis of N-benzylpyridinium hexafluoro-antimonate 34.13 g (0.1 mol) of N-benzylpyridinium tosylate obtained in Example 1 was dissolved in 100 of water, and was added to 25.88 g (0.1 mol) of sodium hexafluoroantimonate. The precipitated while solid was washed with ether and dried to give the titled compound. Yield: 72%.

Example 7

Synthesis of N-benzyl-N,N-dimethylanilinium hexafluorophosphate

Analogously to Example 5, the titled compound was obtained from N-benzyl-N,N-dimethylanilinium tosylate obtained in Example 2 and sodium hexafluorophosphate. Yield: 65%.

Example 8

Synthesis of N-(4-methoxybenzyl)-N-ethyl-N-methylanilinium tetrafluoroborate

Analogously to Example 6, the titled compound was obtained from N-(4-methoxybenzyl)-N-ethyl-N-methylanilinium tosylate obtained in Example 4 and sodium tetrafluoroborate. Yield: 55%.

What is claimed is:

1. A method for synthesizing an N-benzylpyridinium sulfonate which comprises reacting in one step a benzyl alcohol of the formula:

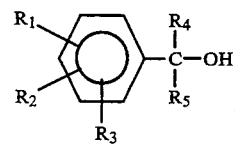

wherein $R_1$, $R_2$ and $R_3$ independently of one another denote hydrogen, hydroxyl, halogen, alkyl, alkoxy, nitro, amino, alkylamino, acyl, cyano, alkoxycarbonyl or carbamoyl, and $R_4$ and $R_5$ independently of one another denote hydrogen, halogen or alkyl, with a benzene- or naphthalenesulfonyl chloride optionally substituted with one or more alkyl groups, and a pyridine of the formula:

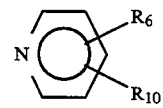

wherein $R_6$ and $R_{10}$ independently of one another denote hydrogen, hydroxyl, halogen, alkyl, alkoxy, nitro, amino, alkylamino, acyl, cyano, alkoxycarbonyl or carbamoyl, in the presence of an acid-binding agent to produce an N-benzylpyridinium sulfonate.

2. The method according to claim 1, wherein said acid-binding agent is said pyridine itself, present in excess in the reaction mixture or a secondary amine, a tertiary amine or an alkali metal alcoholate separately added to the reaction mixture.

3. The method according to claim 2, wherein said acid-binding agent is dicyclohexylamine or an alkali metal alcoholate.

4. A method for the synthesis of a quaternary ammonium compound which comprises reacting the N-benzylpyridinium sulfonate product of claim 1 with a compound of the formula MX, wherein M is an alkali metal and X is $AsF_6^-$, $SbF_6^-$, $BF_4^-$, $PF_6^-$, $ClO_4^-$, $FeCl_4^-$ or $CF_3SO_3^-$ anion, to replace said sulfonate anion with said $X^-$ anion.

5. A method for synthesizing an N-benzylanilinium sulfonate which comprises reacting in one step a benzyl alcohol of the formula:

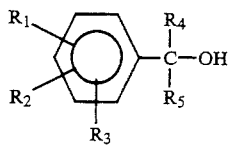

wherein $R_1$, $R_2$ and $R_3$ independently of one another denote hydrogen, hydroxyl, halogen, alkyl, alkoxy, nitro, amino, alkylamino, acyl, cyano, alkoxycarbonyl or carbamoyl, and $R_4$ and $R_5$ independently of one another denote hydrogen, halogen or alkyl, with
 a benzene- or naphthalenesulfonyl chloride, and
 an aniline derivative of the formula

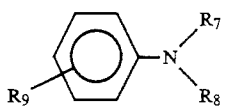

wherein $R_7$ and $R_8$ independently of one another denote alkyl or alkenyl, and $R_9$ denotes hydrogen, hydroxyl, halogen, alkyl, alkoxy, nitro, amino, alkylamino, acyl, cyano, alkoxycarbonyl or carbamoyl,
 in the presence of an acid-binding agent to produce an N-benzylanilinium sulfonate.

6. The method according to claim 5, wherein said acid-binding agent is said aniline derivative itself present in excess in the reaction mixture or a secondary amine, a tertiary amine or an alkali metal alcoholate separately added to the reaction mixture.

7. The method according to claim 6, wherein said acid binding agent is dicyclohexylamine or an alkali metal alcoholate.

8. A method for the synthesis of a quaternary ammonium compound which comprises reacting the N-benzylanilinium sulfonate product of claim 5 with a compound of the formula MX, wherein M is an alkali metal and X is $AsF_6^-$, $SbF_6^-$, $BF_4^-$, $PF_6^-$, $ClO_4^-$, $FeCl_4^-$ or $CF_3SO_3SO_3^-$ anion, to replace said sulfonate anion with said $X^-$ anion.

* * * * *